United States Patent
Wood et al.

(10) Patent No.: US 7,754,192 B2
(45) Date of Patent: Jul. 13, 2010

(54) CATIONIC POLYMERS AND THE USE THEREOF IN COSMETIC FORMULATIONS

(75) Inventors: Claudia Wood, Weinheim (DE); Maximilian Angel, Schifferstadt (DE); Lysander Chrisstoffels, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1217 days.

(21) Appl. No.: 10/506,871

(22) PCT Filed: Mar. 13, 2003

(86) PCT No.: PCT/EP03/02577

§ 371 (c)(1), (2), (4) Date: Sep. 3, 2004

(87) PCT Pub. No.: WO03/080001

PCT Pub. Date: Oct. 2, 2003

(65) Prior Publication Data
US 2005/0084469 A1   Apr. 21, 2005

(30) Foreign Application Priority Data
Mar. 21, 2002 (DE) ............... 102 12 705
Jun. 19, 2002 (DE) ............... 102 27 500

(51) Int. Cl.
*A61Q 5/00* (2006.01)
(52) U.S. Cl. .................. 424/70.11; 424/70.1
(58) Field of Classification Search ........ None
See application file for complete search history.

(56) References Cited

U.S. PATENT DOCUMENTS 4,048,301 A * 9/1977 Papantoniou
4,240,450 A * 12/1980 Grollier et al.
4,380,600 A * 4/1983 Hosoda et al. ............ 524/458
5,223,247 A * 6/1993 Kopolow et al. ........... 424/47
6,964,774 B1 * 11/2005 Dieing et al. ............. 424/401

FOREIGN PATENT DOCUMENTS

JP    2001-181354    *   7/2001

OTHER PUBLICATIONS

English Translation of JP 2001-181354, 2001.*
Sodium Chloride MSDS, downloaded from the world wide web on Dec. 17, 2009.*
Von H. Fikentscher, "Systematik der cellulosen auf grund ihrer viskosität in lösung", Cellulosechemie, vol. 13, pp. 58-64 1932.*
Von H. Fikentscher, "Systematik der cellulosen auf grund ihrer viskosität in lösung", Cellulosechemie, vol. 13, pp. 71-74 1932.*
William C. Griffin, "Calculation of HLB values of non-ionic surfactants", Journal of the Society of Cosmetic Chemists, vol. 5, pp. 249-256 1954.*
Antje Lieske, et al., "Synthesis and characterization of block copolymers containing cationic blocks", Macromol,Chem. Phys., vol. 199, pp. 255-260 1998.*
Ullmann's Encyclopedia of Industrial Chemistry, vol. A21, Kapitel "Polyacrylates", 5. Edition, pp. 157-178 1992.*

* cited by examiner

*Primary Examiner*—Michael G Hartley
(74) *Attorney, Agent, or Firm*—Oblon, Spivak, McClelland, Maier & Neustadt, L.L.P.

(57) ABSTRACT

The present invention relates to cationic polymers, to processes for the preparation thereof, and to the use thereof in cosmetic formulations.

19 Claims, No Drawings

CATIONIC POLYMERS AND THE USE THEREOF IN COSMETIC FORMULATIONS

The present invention relates to cationic polymers, to processes for the preparation thereof, and to the use thereof in cosmetic formulations. The cationic graft polymers are obtainable by polymerization of quaternized-cationic, free-radically polymerizable monomers and optionally further free-radically copolymerizable monomers in the presence of a polyether-containing compound with the proviso that the reaction takes place in the presence of small amounts of water of less than 20% by weight of the total reaction mixture.

DE 197 14 714 A1 describes linear block polymers of polyethylene glycol and cationic monomers which are synthesized using macroinitiators. The compounds are used as polymeric surfactants. Grafting reactions which lead to branched polymers are not described and for the process described to be neglected, according to a statement by the inventors (Lieske A and Jaeger W (1998) Macromol Chem Phys 199:255-260; see in particular p. 256; left-hand column, final paragraph: "Side reactions, particularly grafting onto the PEG chain and transfer reactions leading to DADMAC homopolymer, are neglectable").

DE-A 29 24 663 and U.S. Pat. No. 4,380,600 describe the free radical polymerization of ethylenically unsaturated monomers in aqueous solution using water-soluble polymers as dispersants. The water-soluble polymer used is, inter alia, polyethylene glycol. The ethylenically unsaturated monomer used is also a quaternary ammonium compound. The process described is a water-in-water ("W/W") emulsion polymerization which has considerable water fractions. Thus, the ethylenically unsaturated monomers are used in a weight ratio of from 3 to 150 parts per 100 parts of water. The weight ratio of ethylenically unsaturated monomer to the water-soluble polymer (e.g. polyethylene glycol) is 1:5 to 5:1. The high water fraction means that, when the process is carried out in this way, none or only a very small part of the grafting of the ethylenically unsaturated monomers takes place onto the water-soluble polymer. The water-soluble polymer (e.g. polyethylene glycol) here has the function of a dispersant for the aqueous dispersion.

EP-A 0 183 466 describes processes for the polymerization of water-soluble monomers in aqueous solution in the presence of a dispersant and a salt. A dispersant which may be used is, inter alia, polyethylene glycol. Water-soluble monomers include certain cationic monomers. The high water content typical of a "W/W" emulsion polymerization means that, when the process is carried out in this way, none or only a very small part of the grafting of the ethylenically unsaturated monomers takes place onto the water-soluble polymer. The water-soluble polymer (e.g. polyethylene glycol) here has the function of a dispersant. A grafting of the monomers onto the dispersant is not mentioned. The resulting compounds are used as flocculants for wastewater treatment or in the paper industry. Use in cosmetic preparations is not described.

EP-A1 0 880 548 and DE 195 21 096 A1 describe processes for the preparation of dispersions of water-soluble vinyl polymers and stabilizers for carrying out the process. The stabilizers described are graft polymers consisting of a backbone of polyethylene oxide and graft branches of cationic, preferably quaternary, vinyl polymers. Synthesis of the stabilizer as described in example 1 takes place in aqueous solution. The weight ratio of ethylenically unsaturated monomer:polyethylenei glycol:water are 24:30:270. A use of these stabilizers in cosmetic preparations is not mentioned. A disadvantage of the process described is the high water content in the reaction mixture. When the process is carried out in this way, none or only a very small part of the grafting of the ethylenically unsaturated monomers takes place onto the water-soluble polymer, i.e. polymers of the cationic monomer and polyethylene glycol are present alongside one another to a considerable degree individually without grafting (cf. statement in Lieske A & Jaeger W (1998) Macromol Chem Phys 199:255-260; see above). This impairs the quality of the product, in particular its suitability in cosmetics. Polyethylene glycol here has the function of a dispersant.

EP-A 1 123 942 describes the polymerization of anionic (carboxylic) ethylenically unsaturated monomers in a melt of polyethylene glycol. The carboxyl groups present in the polymer are then reacted at least partially by adding an alkyleneimine. In this connection, primary amino groups are preferably obtained. Secondary amino groups are also possible in some instances. Tertiary or quaternary amino groups are not described and are not accessible by the claimed process either.

DD 117 326 describes the preparation of quaternized graft polymers by means of a two-stage process. Firstly, a polymerization of nonionic ethylenically unsaturated monomers (3-chloro-2-hydroxypropyl acrylate or vinylimidazole) takes place in a melt of polyethylene glycol. The quaternization takes place starting from the resulting polymer in a second step by reaction with triethylamine or methyl iodide. The polymers are used in the preparation of photographic gelatin-silver halide emulsion layers. Use in the field of cosmetics is not described. The described process has disadvantages from an economic and process technology viewpoint. Firstly, process control is complex due to the process being in two stages. Secondly, the process may, for example as a result of an incomplete second reaction step, lead to polymers with non-reproducible properties. The second reaction step additionally sometimes requires toxic compounds which further hinder the preparation and, particularly when the polymer is used, for example, in the cosmetics field, necessitate purification.

WO 00/49998 describes polymerization processes of vinyl esters in polyether-containing compounds, such as, for example, polyethylene glycol. In addition, further monomers such as cationic monomers can optionally be used. The process includes the subsequent saponification of the polymer. In the polymers described, the proportion of the monomers which are additionally optionally used is limited to a maximum of 50% (see page 9/line 32 ff.). It is preferably 0 to 20%.

U.S. Pat. No. 3,990,459 describes cosmetic compositions which comprise grafted cationic polymers. Said grafted cationic polymers are obtained by copolymerization of from 3 to 95% by weight of dimethylaminoethyl methacrylate, 2 to 50% by weight of polyethylene glycol contained and 3 to 95% by weight of a further monomer, such as, for example, N-vinylpyrrolidone. Quaternization of dimethylaminoethyl methacrylate can be undertaken, for example, with dimethyl sulfate. According to the claim, in the polymers described here, the polyethylene glycol fraction is not greater than 50% by weight. In the examples according to the invention, it is even significantly less than this, at 10% by weight.

U.S. Pat. No. 4,408,301 describes shampoo compositions which comprise grafted cationic polymers. Said grafted cationic polymers are obtained by copolymerization of from 3 to 95% by weight of N-vinylpyrrolidone, 3 to 95% by weight of dimethylaminoethyl methacrylate and 2 to 50% by weight of polyethylene glycol. Quaternization of dimethylaminoethyl methacrylate can be undertaken, for example, with dimethyl sulfate. According to the claim, in the polymers described here, the polyethylene glycol fraction is not greater than 50% by weight. In the examples according to the invention, it is even significantly less than this, at 8.15% by weight and 8.81% by weight.

DE 2 623 692 describes hair colorants which comprise grafted cationic polymers. Said grafted cationic polymers are obtained by copolymerization of N-vinylpyrrolidone, dimethylaminoethyl methacrylate and polyethylene glycol. Quaternization of dimethylaminoethyl methacrylate can be undertaken, for example, with dimethyl sulfate. Preferably, the graft polymers are obtained by copolymerization of from 3 to 95% by weight of N-vinylpyrrolidone, 3 to 95% by weight of dimethylaminoethyl methacrylate and 2 to 50% by weight of polyethylene glycol. According to the claim, in the polymers described here, the polyethylene glycol fraction is not greater than 50% by weight. In the examples according to the invention, it is even considerably less than this, at 8.15% and 8.81% by weight.

To condition and hold keratin substances such as hair, nails and skin, use has also been made of synthetic polymers for a long time. Requirements for hair conditioning agents are, for example, a marked reduction in the required combing force in wet and also in dry hair, good detangling upon first combing and good compatibility with other formulation components. Requirements for hair-setting resins are, for example, a strong hold at high atmospheric humidity, elasticity, ability to be washed out of the hair and compatibility with other formulation components. The combination of different properties leads to difficulties. For example, polymers with good setting properties often exhibit low elasticities, meaning that, upon mechanical stress of the hairstyle, the setting action is often considerably impaired as a result of damage to the polymer film. In addition, synthetic polymers are used in cosmetic formulations which comprise pigments or cosmetically effective active components, as compatibility promoters for achieving a homogeneous, stable formulation.

Despite extensive efforts, there continues to be a need for improving polymers for producing elastic hairstyles coupled with simultaneously strong hold even in high atmospheric humidity, good ability to be washed out and good feel of the hair. The need for improvements consists likewise in the case of polymers for generating hair which can easily be combed and detangled and for conditioning the skin and hair, in their sensorily registerable properties such as feel, volume, handleability etc. Also desirable are clear aqueous preparations of these polymers which are accordingly characterized by good compatibility with other formulation constituents.

It is an object of the invention to provide novel polymers for, in particular, hair cosmetic formulations which, on the one hand, impart strong hold coupled with high elasticity to the hairstyle and, on the other hand, impart good combability coupled with voluminous appearance to the hair, and produce clear preparations with water.

We have found that this object is achieved by the provision of the polymers according to the invention.

The invention firstly provides for the use of cationic polymers obtainable by polymerization of
  from 3 to 30% by weight of at least one quaternary nitrogen-containing free-radically polymerizable monomer (a1) and/or a direct preproduct (a2) thereof
  in the presence of from 70 to 97% by weight of at least one polyether-containing compound (b) and
  optionally from 0 to 15% by weight of one or more further free-radically polymerizable monomers (c) with a solubility in water above 60 g/l at 25° C. and
  optionally from 0 to 15% by weight of one or more further free-radically polymerizable monomers (d) with a solubility in water of less than 60 g/l at 25° C.
  where the water content in the reaction mixture during the polymerization is less than 20% by weight, and where, in the case of the use of a preproduct (a2), this is converted at least partially into a compound containing quaternary nitrogen (a2') subsequently to or during the polymerization, where the molar ratio of the sum of the monomers (a1), (a2') and (c) to the sum of the monomers (d) is at least 2 to 1, and where the percentages by weight of the individual components a1 and/or a2, b and optionally c and d add up in each case to 100% by weight
in cosmetic preparations.

The invention further provides polymers obtainable by polymerization of
  from 3 to 30% by weight of at least one cationic, quaternary, free-radically polymerizable monomer (a1) and
  in the presence of from 70 to 97% by weight of at least one polyether-containing compound (b) and
  optionally from 0 to 15% by weight of one or more further free-radically polymerizable monomers (c) with a solubility in water above 60 g/l at 25° C. and
  optionally from 0 to 15% by weight of one or more further free-radically polymerizable monomers (d) with a solubility in water below 60 g/l at 25° C.,
  where the molar ratio of the sum of the monomers (a1) and (c) to the sum of the monomers (d) is at least 2 to 1, where the water content in the reaction mixture during the polymerization is less than 20% by weight, and where the percentages by weight of the individual components a1, b and optionally c and d add up in each case to 100% by weight.

Also included is the use of said polymers according to the invention in applications listed below, in particular in cosmetic preparations.

The invention further provides processes for the preparation of the polymers according to the invention, which comprises polymerizing
  from 3 to 30% by weight of at least one cationic, quaternary free-radically polymerizable monomer (a1)
  in the presence of from 70 to 97% by weight of at least one polyether-containing compound (b) and
  optionally from 0 to 15% by weight of one or more further free-radically polymerizable monomers (c) with a solubility in water of more than 60 g/l at 25° C. and
  optionally from 0 to 15% by weight of one or more further free-radically polymerizable monomers (d) with a solubility in water of less than 60 g/l at 25° C.,
  where the molar ratio of the sum of the monomers (a1) and (c) to the sum of the monomers (d) is at least 2 to 1, where the water content in the reaction mixture during the polymerization is less than 20% by weight, and where the percentages by weight of the individual components a1, b and optionally c and d add up in each case to 100% by weight.

The polymers according to the invention have excellent dry and wet combability of the hair treated therewith. Further advantages are, inter alia, the soft feel and the antistatic properties of the surfaces treated therewith, such as textiles, hair, skin, paper, fiber materials and nonwoven materials, and also other surfaces. Pigment-containing or preparations containing cosmetically effective active components are stabilized by the polymers. A further advantage is that using the polymers according to the invention it is possible to formulate aqueous compositions such as hair shampoos and washing gels to be in clear form. Moreover, the polymers can be used in the form of aqueous or aqueous/alcoholic solutions, as aqueous emulsion, microemulsion, dispersion, opaque or transparent gels or aerosols.

Of essential importance for the excellent conditioning properties is the content of at least 70% by weight of polyether-containing compounds in the polymers according to the invention, which are thereby significantly different to the polymers disclosed in U.S. Pat. No. 3,990,459, U.S. Pat. No. 4,048,301 and DE 26 23 692. The polymers described therein are significantly inferior to those according to the invention, for example with regard to the decrease in combing force in the case of hair cosmetic applications (see comparative example 3).

In the preparation of the polymers used according to the invention, grafting onto the polyether-containing compounds (b) may occur during the polymerization, which may lead to the advantageous properties of the polymers. Depending on the degree of grafting, the polymers used according to the invention are to be understood as meaning either pure graft polymers or mixtures of the abovementioned graft polymers with nongrafted polyether-containing compounds and homo- or copolymers of the monomers (a1) and optionally (a2), (c) and (d). In this connection, the polymers according to the invention are markedly superior with regard to their properties to mixtures in which the polymerization is realized in the presence of relatively large amounts of water (see comparative experiment 1) or in which the polyether component is only added after the polymerization of the monomers (see comparative experiment 2). However, mechanisms other than grafting are also conceivable which can bring about these changed advantageous properties.

The polyether-containing compounds (b) used may be either polyalkylene oxides based on ethylene oxide, propylene oxide, butylene oxide and other alkylene oxides, or polyglycerol.

Depending on the nature of the monomer building blocks, the polymers contain the following structural units.

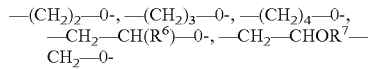

where $R^6$ is $C_1$-$C_{24}$-alkyl;

$R^7$ is hydrogen, $C_1$-$C_{24}$-alkyl, $R^6$—C(=O)—, $R^6$—NH—C(=O)—.

In this connection, the structural units may be either homopolymers or random copolymers and block copolymers.

As polyether (b), preference is given to using polymers of the formula I,

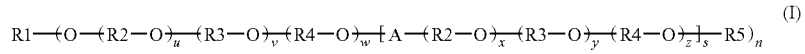

in which the variables, independently of one another, have the following meanings:

$R^1$ is hydrogen, $C_1$-$C_{24}$alkyl, $R^6$—C(=O)—, $R^6$—NH—C(=O)—, polyalcohol radical;

$R^5$ is hydrogen, $C_1$-$C_{24}$-alkyl, $R^6$—C(=O)—, $R^6$—NH(=O)—;

$R^2$ to $R^4$
  independently of one another are —(CH$_2$)$_2$—, —(CH$_2$)$_3$—, —(CH$_2$)$_4$—, —CH$_2$—CH(R$^6$)—, —CH$_2$—CHOR$^7$—CH$_2$—;

$R^6$ is $C_1$-$C_{24}$-alkyl;

$R^7$ is hydrogen, $C_1$-$C_{24}$-alkyl, $R^6$—C(=O)—, $R^6$—NH—C(=O)—;

A is —C(=O)—O, —C(=O)—B—C(=O)—O, —CH$_2$—CH(—OH)—B—CH(—OH)—CH$_2$—O, —C(=O)—NH—B—NH—C(=O)—O,

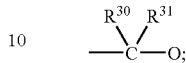

B is —(CH$_2$)$_t$—, arylene, optionally substituted;

$R^{30}$, $R^{31}$
  independently of one another are hydrogen, $C_1$-$C_{24}$-alkyl, $C_1$-$C_{24}$-hydroxyalkyl, benzyl or phenyl;

n is 1 when $R^1$ is not a polyalcohol radical or
n is 1 to 1 000 when $R^1$ is a polyalcohol radical
s is 0 to 1 000;
t is 1 to 12;
u is 1 to 5 000;
v is 0 to 5 000;
w is 0 to 5 000;
x is 0 to 5 000;
y is 0 to 5 000;
z is 0 to 5 000.

The terminal primary or secondary hydroxyl groups of the polyethers prepared on the basis of polyalkylene oxides, and the secondary OH groups of polyglycerol may be present freely in unprotected form, or else etherified or esterified with alcohols, such as, for example, mono-, di-, tri- or polyalcohols, of chain length $C_1$-$C_{24}$ or with carboxylic acids of chain length $C_1$-$C_{24}$, and optionally crosslinked, or reacted with isocyanates, diisocyanates or triisocyanates to give urethanes and optionally crosslinked.

Alkyl radicals for $R^1$ and $R^5$ to $R^7$ which may be mentioned are branched or unbranched $C_1$-$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$ to $C_{12}$-alkyl chains, particularly preferably $C_1$ to $C_6$-alkyl chains.

The molecular weight of the polyethers is in the range below 1 000 000 (number-average), preferably in the range from 300 to 100 000, particularly preferably in the range from 500 to 50 000, very particularly preferably in the range from 600 to 20 000.

Homopolymers of ethylene oxide or copolymers of ethylene oxide and propylene oxide are particularly preferred, where the molar ratio of ethylene oxide to propylene oxide is preferably in a range from 1:9 to 9:1. Advantageously, homopolymers of ethylene oxide or copolymers with an ethylene oxide content of from 9 to 99 mol % are used. For the ethylene oxide polymers which are preferably to be used, the content of copolymerized ethylene oxide is thus 10 to 100 mol %. Suitable comonomers for these copolymers are propylene oxide, butylene oxide and/or isobutylene oxide. For example, copolymers of ethylene oxide and propylene oxide, copolymers of ethylene oxide and butylene oxide, and copolymers of ethylene oxide, propylene oxide, and at least one butylene oxide are suitable. The ethylene oxide content of the copolymers is preferably 10 to 99 mol %, the propylene oxide content is 1 to 90 mol % and the content of butylene oxide in the copolymers is 1 to 30 mol %. In addition to straight-chain homo- or copolymers, it is also possible to use branched homo- or copolymers as polyether-containing compounds (b).

Branched polymers can be prepared by an addition reaction onto, for example, polyalcohol radicals, e.g. onto pentaerythritol, glycerol or onto sugar alcohols, such as D-sorbitol and D-mannitol, but also onto polysaccharides, such as cellulose and starch, ethylene oxide and optionally also propylene oxide and/or butylene oxides. The alkylene oxide units may be distributed randomly or be in the form of blocks within the polymer.

It is, however, also possible to use polyesters of polyalkylene oxides and aliphatic or aromatic dicarboxylic acids, e.g. oxalic acid, succinic acid, adipic acid and terephthalic acid with molar masses of from 1 500 to 25 000, as described, for example, in EP-A-0 743 962, as polyether-containing compound. In addition, it is also possible to use polycarbonates by reaction of polyalkylene oxides with phosgene or carbonates, such as, for example, diphenyl carbonate, and also polyurethanes by reaction of polyalkylene oxides with aliphatic and aromatic diisocyanates.

Particularly preferred polyethers (b) are polymers of the formula I with an average molecular weight of from 300 to 100 000 (number-average) in which the variables, independently of one another, have the following meanings:

$R^1$ is hydrogen, $C_1$-$C_{12}$-alkyl, $R^6$—C(=O)—, $R^6$—N(=O)—, polyalcohol radical;

$R^5$ is hydrogen, $C_1$-$C_{12}$-alkyl, $R^6$—C(=O)—, $R^6$—NH—C(=O)—;

$R^2$ to $R^4$
are —(CH$_2$)$_2$—, —(CH$_2$)$_3$—, —(CH$_2$)$_4$—, —CH$_2$—CH(R$^6$)—, —CH$_2$—CHOR$^7$—CH$_2$—;

$R^6$ is $C_1$-$C_{12}$-alkyl;

$R^7$ is hydrogen, $C_1$-$C_{12}$-alkyl, $R^6$—C(=O)—, $R^6$—NH—C(=O)—;

n is 1 when $R^1$ is not a polyalcohol radical or n is 1 to 8 when $R^1$ is a polyalcohol radical s is 0;

u is 2 to 2 000;

v is 0 to 2 000;

w is 0 to 2 000.

Very particularly preferred polyethers (b) are polymers of the formula I with an average molecular weight of from 600 to 20 000 (number-average) in which the variables, independently of one another, have the following meanings:

$R^1$ is hydrogen, $C_1$-$C_6$-alkyl, $R^6$—C(=O)—, $R^6$—NH—C(=O)—;

$R^5$ is hydrogen, $C_1$-$C_6$-alkyl, $R^6$—C(=O)—, $R^6$—NH—C(=O)—;

$R^2$ to $R^4$
are —(CH$_2$)$_2$—, —(CH$_2$)$_3$—, —(CH$_2$)$_4$—, —CH$_2$—CH(R$^6$)—, —CH$_2$—CHOR$^7$—CH$_2$—;

$R^6$ is $C_1$-$C_6$-alkyl;

$R^7$ is hydrogen, $C_1$-$C_6$-alkyl, $R^6$—C(=O)—, $R^6$—NH—C(=O)—;

n is 1;

s is 0;

u is 5 to 500;

v is 0 to 500;

w is 0 to 500.

However, other polyethers which may be used are silicone derivatives. Suitable silicone derivatives are the compounds known under the INCI name Dimethicone Copolyols or silicone surfactants, such as, for example, those available under the tradenames Abil® (T. Goldschmidt), Alkasil® (Rhône-Poulenc), Silicone Polyol Copolymer® (Genesee), Belsil® (Wacker), Silwet® (Witco, Greenwich, Conn., USA) or Dow Corning (Dow Corning). These include compounds with the CAS numbers 64365-23-7; 68937-54-2; 68938-54-5; 68937-55-3.

Silicones are used in hair cosmetics generally to improve the feel. The use of polyether-containing silicone derivatives as polyether (b) in the polymers according to the invention can therefore additionally lead to an improvement in the feel of the hair.

Preferred representatives of such polyether-containing silicone derivatives are those which contain the following structural elements:

(II)

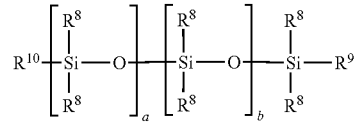

where:

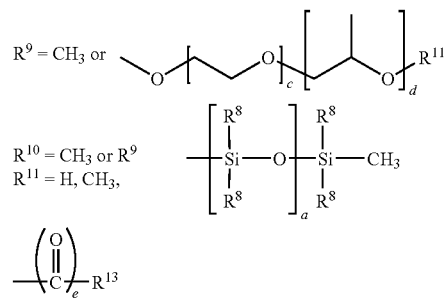

$R^{13}$ is an organic radical having 1 to 40 carbon atoms, which can contain amino, carboxylic acid or sulfonate groups or, when e=0, also means the anion of an inorganic acid, and where the radicals $R^8$ may be identical or different, and either originate from the group of aliphatic hydrocarbons having 1 to 20 carbon atoms, are cyclic aliphatic hydrocarbons having 3 to 20 carbon atoms, are of an aromatic nature or are identical to $R^{12}$, where:

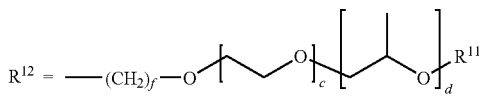

with the proviso that at least one of the radicals $R^8$, $R^9$ or $R^{10}$ is a polyalkylene oxide-containing radical in accordance with the abovementioned definition, and f is an integer from 1 to 6, a and b are integers such that the molecular weight of the polysiloxane block is between 300 and 30 000, c and d may be integers between 0 and 50 with the proviso that the sum of c and d is greater than 0, and e is 0 or 1.

Preferred radicals $R^9$ and $R^{12}$ are those in which the sum c+d is between 5 and 30.

The groups $R^8$ are preferably chosen from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals, such as benzyl or phenylethyl, and tolyl and xylyl and $R^{12}$.

Particularly suitable radicals $R^{11}$ are those in which, when $R^{11}=-(CO)_e-R^{13}$, $R^{13}$ is any alkyl, cycloalkyl or aryl radical which has between 1 and 40 carbon atoms and which may carry further ionogenic groups such as $NH_2$, COOH, $SO_3H$.

Preferred inorganic radicals $R^{13}$ are, when e=0, phosphate and sulfate.

Particularly preferred polyether-containing silicone derivatives are those of the structure:

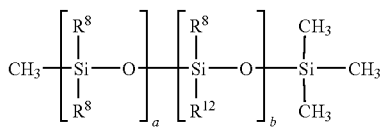

Furthermore, other polyethers (b) which may be used are homo- and copolymers of polyalkylene oxide-containing ethylenically unsaturated monomers, such as, for example, polyalkylene oxide (meth)acrylates, polyalkylene oxide vinyl ether, polyalkylene oxide (meth)acrylamides, polyalkylene oxide allylamides or polyalkylene oxide vinylamides. It is, of course, also possible to use copolymers of such monomers with other ethylenically unsaturated monomers.

Other polyether-containing compounds b) which may be used are, however, reaction products of polyethyleneimines with alkylene oxides. The alkylene oxides used in this case are preferably ethylene oxide, propylene oxide, butylene oxide and mixtures of these, particularly preferably ethylene oxide. As polyethyleneimines it is possible to use polymers with number-average molecular weights of from 300 to 20 000, preferably 500 to 10 000, very particularly preferably 500 to 5 000. The weight ratio between alkylene oxide used and polyethyleneimine is in the range from 100:1 to 0.1:1, preferably in the range 50:1 to 0.5:1, very particularly preferably in the range 20:1 to 0.5:1.

The polyether (b) is most preferably a homopolymer of ethylene oxide or a block copolymer of ethylene oxide/propylene oxide with a molecular weight of less than 100 000 g/mol, preferably less than 20 000 g/mol. The blocks can be in the form A-B or A-B-A or B-A-B or other combinations.

For the polymerization in the presence of the polyethers (b), the component (a1) used is a free-radically polymerizable monomer with at least one quaternary nitrogen. For the purposes of this invention, quaternary nitrogen means nitrogen to which four organic radicals are covalently bonded. By way of example, suitable monomers containing a quaternary nitrogen which may be mentioned are:

1) Quaternary vinylamines of the formulae (IIIa) and (IIIb) and salts thereof:

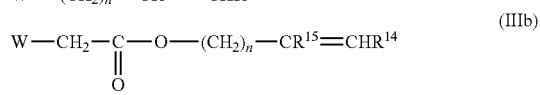

where:
$R^{14}$ and $R^{15}$, independently of one another, are chosen from the group consisting of hydrogen, $C_1$-$C_8$ linear- or branched-chain alkyl, methoxy, ethoxy, 2-hydroxyethoxy, 2-methoxyethoxy and 2-ethoxyethyl. Preference is given to hydrogen, methyl or ethyl, n is 0, 1 or 2, W is $-\overset{+}{N}(R^{16})_3/X^-$ or

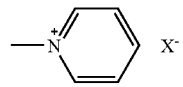

where the radicals $R^{16}$ may be chosen to be identical or different from the group consisting of $C_1$-$C_{40}$ linear- or branched-chain alkyl radicals, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl, preferably methyl, ethyl and n-propyl, $X^-$ is an anion, preferably an anion which is cosmetically compatible. Preferred anions are acetate, methylsulfate or halide, such as, in particular, chloride or bromide.)

2) Quaternary N,N,N-trialkylaminoalkyl acrylates and methacrylates and quaternary N,N,N-trialkylaminoalkylacrylamides and -methacrylamides of the formula (IV) and salts thereof

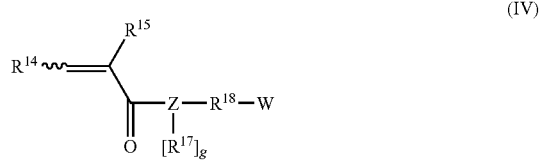

where $R^{14}$, $R^{15}$ and W have the same meanings as in the formula IIIa and IIIb, and $R^{17}$=hydrogen or methyl, $R^{18}$=alkylene or hydroxyalkylene having 1 to 24 carbon atoms, optionally substituted by alkyl, preferably $C_2H_4$, $C_3H_6$, $C_4H_8$, $CH_2-CH(OH)-CH_2$ g=0 or 1

Z=nitrogen when g=1 or oxygen when g=0.

The amides included according to the invention may be unsubstituted, N-alkyl- or N-alkylamino-monosubstituted or N,N-dialkyl-substituted or N,N-dialkylamino-disubstituted, in which the alkyl or alkylamino groups are derived from $C_1$-$C_{40}$ linear, $C_3$-$C_{40}$ branched-chain, or $C_3$-$C_{40}$-carbocyclic units.

Preferred monomers of the formula (IV) are the salts of N,N,N-trimethylaminomethyl (meth)acrylate, N,N,N-triethylaminomethyl (meth)acrylate, N,N,N-trimethylaminoethyl (meth)acrylate, N,N,N-triethylaminoethyl (meth)acrylate, N,N,N-trimethylaminobutyl (meth)acrylate, N,N,N-triethylaminobutyl (meth)acrylate, N,N,N-trimethylaminohexyl (meth)acrylate, N,N,N-trimethylaminooctyl (meth)acrylate, N,N,N-trimethylaminododecyl (meth)acrylate.

Also preferred are the salts of N-[3-(trimethylamino)propyl]methacrylamide and N-[3-(trimethylamino)propyl]acrylamide, N-[3-(dimethylamino)butyl]methacrylamide, N-[8-(trimethylamino)octyl]methacrylamide, N-[12-(trimethylamino)dodecyl]methacrylamide, N-[3-(triethylamino)propyl]methacrylamide and N-[3-(triethylamino)propyl]acrylamide.

Preference is also given to (meth)acryloyloxyhydroxypropyltrimethylammonium chloride and (meth)acryloyloxyhydroxypropyltriethylammonium chloride.

Very particular preference is given to N,N,N-trimethylaminoethyl methacrylate and N-[3-(trimethylamino)propyl]methacrylamide.)

3) Quaternary N-vinylimidazoles of the formula (V) and salts thereof,

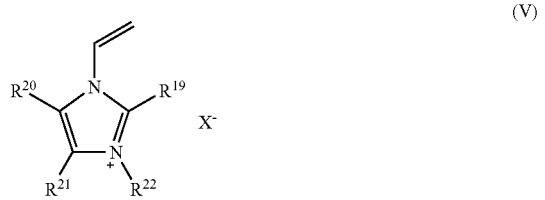

where
$R^{19}$ to $R^{21}$, independently of one another, are hydrogen, $C_1$-$C_4$-alkyl, $C_1$-$C_4$-hydroxyalkyl or phenyl; and
$R^{22}$ is $C_1$-$C_4$-alkyl, $C_1$-$C_4$-hydroxyalkyl or phenyl; and
and $X^-$ is an anion, preferably an anion which is cosmetically compatible. Preference is given to the anions acetate, methylsulfate or halide such as, in particular, chloride or bromide.

Particular preference is given to 3-methyl-1-vinylimidazolium chloride, 3-methyl-1-vinylimidazolium methylsulfate.

4) Quaternary vinylpyridines of the formula (VI) and salts thereof, $R^{21}$, $R^{22}$ and $X^-$ have the same meanings as in formula V.

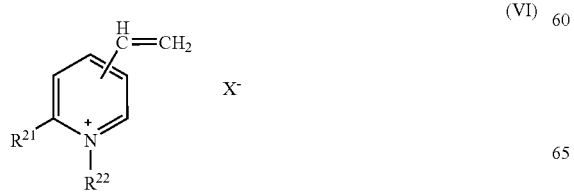

5) Further suitable monomers are diallylamines of the formula (VII) and salts thereof

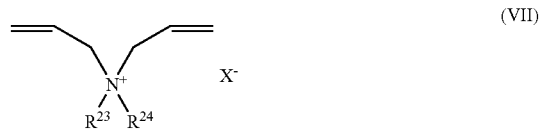

where $R^{23}$ and $R^{24}$ in each case and independently of one another may be $C_1$- to $C_{24}$-alkyl, and $X^-$ has the same meaning as in formula (V). Particular preference is given to N,N-dimethyl-N,N-diallylammonium chloride.

It is of course also possible to polymerize mixtures of different monomers (a1) from the abovementioned groups with one another (and optionally, further monomers).

Particular preference is given to 3-methyl-1-vinylimidazolium chloride, 3-methyl-1-vinylimidazolium methylsulfate and N,N-dimethyl-N,N-diallylammonium chloride, and mixtures of the abovementioned compounds. Of very particular preference for (a1) are mixtures of 3-methyl-1-vinylimidazolium methylsulfate and N,N-dimethyl-N,N-diallylammonium chloride.

Direct preproducts (a2) for component (a1) generally include all those free-radically polymerizable monomers which can be converted to a free-radically polymerizable monomer with a quaternary nitrogen by one conversion. For the subsequently resulting compounds (a2'), the same definitions as given above for (a1) apply. For the component (a2) suitable as direct preproduct for (a1), mention may preferably be made of the following free-radically polymerizable monomers:

1) Unsaturated primary, secondary or tertiary amines

The quaternization of the amines which leads to the polymers according to the invention can, for example, be realized by reaction of the amino groups present in the monomers (a2) with alkyl halides having, preferably, 1 to 24 carbon atoms in the alkyl group. Particular preference is given to using methyl chloride, methyl bromide, methyl iodide, ethyl chloride, ethyl bromide, propyl chloride, hexyl chloride, dodecyl chloride, lauryl chloride and benzyl halides, such as, in particular, benzyl chloride and benzyl bromide. Other agents suitable for the quaternization include dialkyl sulfates, such as, in particular, dimethyl sulfate or diethyl sulfate. A quaternization of basic amino groups can also be realized with alkylene oxides such as ethylene oxides or propylene oxides in the presence of acids. In most cases, the agents used for the quaternization are: methyl chloride, dimethyl sulfate or diethyl sulfate. In addition, a reaction with quaternized epichlorohydrin of the formula (XII) is also possible (see below).

Nonlimiting examples of the amines suitable as monomers (a2) which may be mentioned are:

a) aminoalkyl acrylates and methacrylates and aminoalkylacrylamides and -methacrylamides of the formula (VIII)

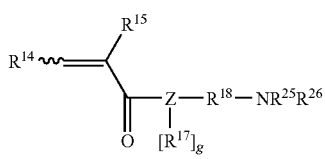

(VIII)

where for $R^{14}$ to $R^{18}$ the definitions given for formula (IV) apply, and $R^{25}$ and $R^{26}$ are in each case and independently of one another chosen from the group consisting of hydrogen, $C_1$-$C_{40}$ linear- or branched-chain alkyl, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl. Preference is given to hydrogen, methyl, ethyl, n-propyl and benzyl.

The amides may be unsubstituted, N-alkyl or N-alkylamino-mono-substituted or N,N-dialkyl-substituted or N,N-dialkylamino-disubstituted, in which the alkyl or alkylamino groups are derived from $C_1$-$C_{40}$ linear, $C_3$-$C_{40}$ branched-chain or $C_3$-$C_{40}$ carbocyclic units. In addition, the alkylamino groups may be quaternized.

Preferred comonomers of the formula (VIII) are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate.

Also preferred are N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide and N-[3-(diethylamino)propyl]acrylamides.

Very particular preference is given to N,N-dimethylaminoethyl methacrylate, N-[3-(dimethylamino)propyl] methacrylamide, N-methylaminoethyl methacrylate, N-[3-(methylamino)propyl]methacrylamide, aminoethyl methacrylate and N-[3-aminopropyl]methacrylamide.

In the case of the abovementioned monomers, a quaternization is preferably carried out using methyl chloride, methyl sulfate or diethyl sulfate.

b) N-Vinylimidazoles of the formula IX, where for $R^{19}$ to $R^{21}$, independently of one another, the definitions given for formula (V) apply.

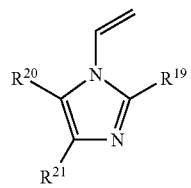

(IX)

Particular preference is given to N-vinylimidazole, 1-vinyl-2-methylvinylimidazole and a quaternization with methyl chloride, methyl sulfate or diethyl sulfate.

c) Diallylamines of the formula (X)

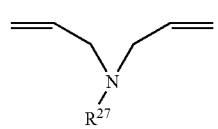

(X)

where $R^{27}$=hydrogen or $C_1$- to $C_{24}$-alkyl. Particular preference is given to N,N-diallylamine and a quaternization with methyl chloride or methyl sulfate.

d) In addition, (a2) can be chosen from compounds such as 1,3-divinylimidazolid-2-one or N-disubstituted vinylamines of the formula (XI):

$$(R^{28})_2N-(CH_2)_n-CR^{15}=CHR^{14} \qquad (XI)$$

where $R^{14}$, $R^{15}$ and n have the same meanings as in the formulae (IIIa) and (IIIb), and the radicals $R^{28}$ can be chosen from the group consisting of hydrogen $C_1$-$C_{40}$ linear- or branched-chain alkyl radicals, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl. Preference is given to methyl, ethyl, n-propyl and benzyl. Here, when n=0, both radicals $R^{28}$ are not hydrogen at the same time.

2) Unsaturated Acids

Quaternary amines can be obtained by reaction of acids, as would be introduced, for example, using unsaturated acids, such as, for example, acrylic acid or methacrylic acid, as starting compound (a2), with a quaternized epichlorohydrin of the formula (XII).

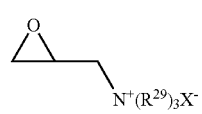

(XII)

Here, $R^{29}$ is preferably $C_1$- to $C_{40}$-alkyl. Preference is given to using 2,3-epoxypropyltrimethylammonium chloride or 3-chloro-2-hydroxypropyltrimethylammonium chloride. The epoxides of the formula XI can also be generated in situ by reaction of the corresponding chlorohydrins with bases, for example sodium hydroxide.

Accordingly, it is also possible to react monomers (a2) containing hydroxyl and/or amino groups. Preference is given to hydroxyl groups of polyvinyl alcohol units and vinylamine units produced by hydrolysis of vinylformamide.

3) Halides of free-radically polymerizable monomers, such as, for example, haloalkyl acrylates or haloalkyl methacrylates. Preference is given to chlorine, bromine or iodine compounds. A nonlimiting example which may be mentioned is 3-chloro-2-hydroxypropyl acrylate. The reaction to give quaternary amines takes place by reaction with amines, e.g. trialkylamines, such as, for example, trimethylamine or triethylamine.

It is of course also possible to polymerize mixtures of the respective monomers from group (a2). Most preferred monomers (a2) include N-vinylimidazole, N,N-diallylamine and aminoethyl methacrylate.

The reaction of the compounds (a2) to give quaternary amines (a2' below) can take place during or after the reaction. If the reaction is carried out subsequently, the intermediate polymer can firstly be isolated or, preferably, reacted directly. The reaction may take place completely or partially. In this connection, preferably at least 10%, particularly preferably at least 50%, especially preferably at least 80%, of the compound (a2) are converted to quaternary amines (a2'). The proportion of the conversion to give quaternary amines is preferably greater the lower the solubility in water of the monomer (a2). If the solubility in water of the monomer (a2) is less than 60 g/l, then the reaction is carried out so that the ratio of the sum of the monomers (a2') and optionally (a1) and (c) to the sum of the monomers (a2) and (d) is at least 2 to 1, preferably 4 to 1, particularly preferably 10 to 1.

The polymerizable monomers (a1) containing the quaternary nitrogen, and/or preproducts (a2) thereof can also be used in a mixture with one or more ethylenically unsaturated copolymerizable comonomers (c) and/or (d), where, in the end product, the molar ratio of the sum of the monomeric units a1 and/or a2 and optionally c to the sum of the monomers d is at least 2 to 1. The ratio is preferably at least 4 to 1, very particularly preferably at least 10 to 1, especially preferably at least 20 to 1.

Suitable monomers (c) are in principle all hydrophilic monomers with a solubility in water above 60 g/l at 25° C. which are copolymerizable with the monomers (a1) and optionally (a2) and (d). These are preferably ethylenically unsaturated monomers. Different monomers suitable as monomers (c) are described, inter alia, in Ullmann's Encyclopedia of Industrial Chemistry, Vol. A21, Chapter "Polyacrylates", pp. 157-178, 5$^{th}$ Edition, 1992, VCH Verlagsgesellschaft mbH, Weinheim, Germany.

The term ethylenically unsaturated means that the monomers have at least one free-radically polymerizable carbon-carbon double bond which may be mono-, di-, tri- or tetra-substituted.

The monomers (c) are preferably
i) N-vinyllactams, preferably with a 5- to 7-membered ring, such as, for example, N-vinylpyrrolidone, N-vinylpiperidone, N-vinylcaprolactam,
ii) acyclic N-vinylcarboxamides, preferably having 2 to 6 carbon atoms, such as, for example, N-vinylformamide, N-ethyl-N-vinylacetamide or N-methyl-N-vinylacetamide,
iii) hydroxyalkyl acrylates, preferably having 2 to 6 carbon atoms, such as, for example, 2-hydroxyethyl acrylate, 2-hydroxyethyl methacrylate, 2-hydroxypropyl methacrylate, butanediol monoacrylate,
iv) ethylenically unsaturated amides, such as, for example, acrylamide or methacrylamide,
v) N-vinylimidazole,
vi) unsaturated acids, preferably carboxylic or sulfonic acids, such as, for example, acrylic acid, maleic acid, methacrylic acid, 2-acrylamido-2-methylpropanesulfonic acid.
vii) unsaturated amines, such as dimethylaminoethyl acrylate, dimethylamino methacrylate.

In addition, it is possible to use any mixtures of different monomers (c). Particularly preferred monomers (c) are N-vinyllactams and N-vinylimidazole. Very particular preference is given to N-vinylpyrrolidone.

Suitable monomers (d) are in principle all hydrophobic monomers with a solubility in water of less than 60 g/l at 25° C. which are copolymerizable with the monomers (a1) and optionally (a2) and (c). These are preferably ethylenically unsaturated monomers. Different monomers suitable as monomers (d) are described, inter alia, in Ullmann's Encyclopedia of Industrial Chemistry, Vol. A21, Chapter "Polyacrylates", pp. 157-178, 5th Edition, 1992, VCH Verlagsgesellschaft mbH, Weinheim, Germany.

These are, in particular,
1) $C_1$-$C_{10}$-alkyl esters of monoethylenically unsaturated $C_3$-$C_6$-carboxylic acids, in particular the esters of acrylic acid and of methacrylic acid. The esters can be derived from $C_1$-$C_{40}$ linear, $C_3$-$C_{40}$ branched-chain or $C_3$-$C_{40}$ carbocyclic alcohols, such as methanol, ethanol, n-propanol, isopropanol, n-butanol, isobutanol, 2-butanol, tert-butanol, n-pentanol, n-hexanol, 2-ethylhexan-1-ol, n-octanol, n-decanol, 2-propylheptan-1-ol, cyclohexanol, 4-tert-butylhexanol or 2,3,5-trimethylcyclohexanol. Particular preference is given to methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl acrylate, stearyl (meth)acrylate. Esters can also be derived from polyfunctional alcohols having 2 to about 8 hydroxyl groups provided they satisfy the solubility requirements for monomers (d). By way of example, mention may be made of esters of ethylene glycol, hexylene glycol, glycerol and 1,2,6-hexanetriol, of aminoalcohols or of alcohol ethers, such as methoxyethanol and ethoxyethanol, (alkyl) polyethylene glycols, (alkyl) polypropylene glycols or ethoxylated fatty alcohols, for example $C_{12}$-$C_{24}$-fatty alcohols reacted with 1 to 200 ethylene oxide units.
2) Di-$C_1$-$C_{10}$-alkyl esters of ethylenically unsaturated dicarboxylic acids, such as maleic acid, fumaric acid or itaconic acid with the $C_1$-$C_{10}$-alkanols or $C_5$-$C_{10}$-cycloalkanols mentioned above under 1), e.g. dimethyl maleate or di-n-butyl maleate.
3) hydrocarbons having at least one free-radically polymerizable carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers. Particular preference is given to vinylaromatic compounds such as styrene and α-methylstyrene which may optionally have one or more substituents on the aromatic ring and which are preferably chosen from $C_1$-$C_4$-alkyl, halogen atoms, in particular chlorine, and/or hydroxyl groups.

4) vinyl, vinylidene or allyl halides, preferably vinyl chloride, vinylidene chloride and allyl chloride.
5) vinyl, allyl and methallyl esters of $C_1$-$C_{40}$ linear, $C_3$-$C_{40}$ branched-chain or $C_3$-$C_{40}$ carbocyclic carboxylic acids of an aliphatic, saturated or unsaturated nature. Examples of preferred carboxylic acids are formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachidic acid, behenic acid, lignoceric acid, cerotinic acid and melissic acid. Preference is given to using vinyl esters of the above-mentioned $C_1$-$C_{12}$-carboxylic acids, in particular of $C_1$-$C_6$-carboxylic acids. Very particular preference is given to vinyl acetate, vinyl propionate, vinyl butyrate, vinyl valerate, vinyl hexanoate, vinyl 2-ethylhexanoate, vinyl decanoate, vinyl laurate and vinyl stearate, and the corresponding allyl and methallyl esters. Vinyl acetate is most preferred.
6) Vinyl, allyl and methallyl ethers of linear or branched, aliphatic alcohols having 2 to 20 carbon atoms, e.g. vinyl methyl ether, vinyl ethyl ether, vinyl dodecyl ether, vinyl hexadecyl ether and vinyl stearyl ether.
7) Monoethylenically unsaturated monocarboxylic acids provided they have a solubility in water of less than 60 g/l at 25° C., such as, for example, acrylamidoglycolic acid, fumaric acid or crotonic acid.

In addition, any desired mixtures of various monomers (d) can be used. Particularly preferred monomers (d) are vinyl acetate, methyl methacrylate, methyl acrylate and ethyl acrylate.

In addition to the abovementioned comonomers, as comonomers (c) or (d) it is also possible to use macromonomers, such as, for example, silicone-containing macromonomers with one or more free-radically polymerizable groups or alkyloxazoline macromonomers, as are described, for example, in EP 408 311. Furthermore, it is also possible to use fluorine-containing monomers, as are described, for example, in EP 558423, compounds which have a crosslinking action or compounds which regulate the molecular weight, in combination or alone. Allocation to groups (c) or (d) is in accordance with their solubility.

It is known to the person skilled in the art that a monomer (a2) can come under the group of monomers (c) or (d) if (a2) has not been converted into a quaternary amine (a2').

The basic monomers (c) or (d) can also be cationized by neutralizing them with mineral acids, such as, for example, sulfuric acid, hydrochloric acid, hydrobromic acid, hydroiodic acid, phosphoric acid or nitric acid, or with organic acids, such as, for example, formic acid, acetic acid, lactic acid or citric acid.

Regulators which can be used are the customary compounds known to the person skilled in the art, such as, for example, sulfur compounds (e.g.: mercaptoethanol, 2-ethylhexyl thioglycolate, thioglycolic acid or dodecyl mercaptan), and tribromochloromethane or other compounds which have a regulating effect on the molecular weight of the resulting polymers.

In some instances, it is also possible to use silicone compounds which contain thiol groups.

Preference is given to using silicone-free regulators.

As monomers (a1), (a2), (c) or (d) it is also possible to use crosslinking monomers, for example compounds with at least two ethylenically unsaturated double bonds, such as, for example, esters of ethylenically unsaturated carboxylic acids, such as acrylic acid or methacrylic acid and polyhydric alcohols, ethers of at least dihydric alcohols, such as, for example, vinyl ethers or allyl ethers. Also suitable are straight-chain or branched, linear or cyclic aliphatic or aromatic hydrocarbons which have at least two double bonds which, in the case of aliphatic hydrocarbons, must not be conjugated. Also suitable are amides of acrylic acid and methacrylic acid and N-allylamines of at least difunctional amines, such as, for example, 1,2-diaminoethane, 1,3-diaminopropane. Also are triallylamine, N-vinyl compounds of urea derivatives, at least difunctional amides, cyanurates or urethanes. Further suitable crosslinkers are divinyldioxane, tetraallylsilane or tetravinylsilane.

Particularly preferred crosslinkers are, for example, methylenebisacrylamide, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

A very particularly preferred crosslinker is divinylethyleneurea.

The crosslinking monomers are used in an amount of less than 5% by weight, based on the total of the starting materials a) to d). Particular preference is given to using less than 3% by weight and very particular preference is given to using less than 1% by weight, of crosslinking monomer.

During the polymerization for the preparation of the polymers according to the invention, it is optionally also possible for other polymers, such as, for example, polyamides, polyurethanes, polyesters, homo- and copolymers of ethylenically unsaturated monomers, to be present. Examples of such polymers, some of which are also used in cosmetics, are the polymers known under the trade names Amerhold™, Ultrahold™, Ultrahold Strong™, Luviflex™VBM, Luvimer™, Acronal™, Acudyne™, Stepanhold™, Lovocryl™, Versatyl™, Amphomer™ or Eastma AQ™. It is also possible to use cationic guar derivatives, such as guar hydroxypropyltrimonium chloride (INCI).

The comonomers (c) and/or (d) according to the invention can, if they contain ionizable groups, be partially or completely neutralized with acids or bases before or after the polymerization in order to adjust, for example, the solubility or dispersibility in water to a desired degree.

Neutralizing agents for monomers which carry acid groups which can be used are, for example, mineral bases, such as sodium carbonate, alkali metal hydroxides, and ammonia, organic bases, such as aminoalcohols, specifically 2-amino-2-methyl-1-propanol, monoethanolamine, diethanolamine, triethanolamine, triisopropanolamine, tri[(2-hydroxy)-1-propyl]amine, 2-amino-2-methyl-1,3-propanediol, 2-amino-2-hydroxymethyl-1,3-propanediol, and diamines, such as, for example, lysine.

To prepare the polymers, the monomers of component a1) can be polymerized in the presence of polyethers either with the help of initiators which form free radicals, or by the action of high-energy radiation, which is also to be understood as including the action of high-energy electrons.

Initiators which can be used for free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl permaleate, cumine hydroperoxide, diisopropyl peroxydicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidonopropane) dihydrochloride or 2-2'- azobis(2-methylbutyronitrile). Also suitable are initiator mixtures or redox initiator systems, such as, for example, ascorbic acid/iron (II) sulfate/sodium peroxodisulfate, tert-butyl hydroperoxide/sodium disulfite, tert-butyl hydroperoxide/sodium hydroxymethanesulfinate.

Preference is given to using organic peroxides.

The amounts of initiator or initiator mixtures used, based on the free-radically polymerizable monomers (a1, a2, c, d) used, are between 0.01 and 100% by weight, preferably between 0.1 and 40% by weight, particularly preferably between 1 and 15% by weight.

The polymerization is carried out in a temperature range from 40 to 200° C., preferably in the range from 50 to 140° C., particularly preferably in the range from 60 to 110° C. It is usually carried out under atmospheric pressure, but can also proceed under reduced or increased pressure, preferably between 1 and 5 bar. The reaction temperature is preferably chosen so that it corresponds at least to the melting temperature of the polyether-containing compound (b) under the reaction conditions in question so that the reaction can be carried out in a melt of (b).

The polymerization can be carried out, for example, as solution polymerization, bulk polymerization, emulsion polymerization, inverse emulsion polymerization, suspension polymerization, inverse suspension polymerization or precipitation polymerization without the methods which can be used being limited thereto. Preference is given to bulk polymerization where the polymerization of a1 and optionally a2, c and/or d is carried out in the presence of b. Here, the content of water in the reaction mixture during the polymerization is less than 20% by weight, preferably less than 15%, particularly preferably less than 10% by weight, especially preferably less than 5% by weight. Preference is given here to working under essentially anhydrous conditions and carrying out a bulk polymerization. In this connection, "essentially anhydrous" means that, apart from the water present in the starting materials, no additional water is introduced into the reaction mixture. In this connection, "during the polymerization" means that the free radical polymerization of the free-radically polymerizable monomers is still not complete. In this connection, a polymerization is regarded as incomplete so long as the content of residual monomers is still greater than 50%, preferably greater than 30%, particularly preferably greater than 10%, very particularly preferably greater than 5%, especially preferably greater than 2%, compared with the starting amount of monomers. When the polymerization is complete in accordance with the above definition, it is possible to add water to the reaction mixture in greater amounts (i.e. in an amount of more than 20% by weight of the reaction mixture).

In the particularly preferred bulk polymerization, the procedure may involve dissolving at least one monomer of group (a1) and/or (a2) and/or any further comonomers of groups (c) and/or (d) in the polyether-containing compound (b) and, after the addition of a polymerization initiator, fully polymerizing the mixture. The polymerization can also be carried out semicontinuously by firstly introducing some, e.g. 10%, of the mixture to be polymerized comprising the polyether-containing compound (b), at least one monomer from group (a1) and/or (a2), any further comonomers of groups (c) and/or (d) and initiator, heating the mixture to polymerization temperature and, after the polymerization has started, adding the remainder of the mixture to be polymerized according to the progress of the polymerization. The polymers can, most preferably, also be obtained by initially introducing the polyether-containing compounds of group (b) into a reactor, heating them to the polymerization temperature and adding at least one monomer of group (a1) and/or (a2), any further comonomers of groups (c) and/or (d) and polymerization initiator either in one portion, batchwise or preferably continuously, and polymerizing the mixture.

For the polymerization, it is possible to add emulsifiers. Examples of emulsifiers are ionic or nonionic surfactants whose HLB value is in the range from 3 to 18. To define the HLB value, reference is made to the publication by Griffin W C (1954) J. Soc. Cosmetic Chem. Volume 5, p. 249. The amount of surfactants, based on the polymer, is 0 to 10% by weight. Preferably, no surfactants are added for the polymerization.

The polymerizations for the preparation of the polymers according to the invention can be carried out in the presence of at least one nonaqueous organic solvent or in mixtures of at least one organic solvent and water. Preference is given to using, per 100 parts by weight of the sum of the starting materials (a1 and/or a2, b, and optionally c and d), 5 to 2 000 parts by weight, preferably 10 to 500 parts by weight, of the organic solvent or the solvent mixture. Examples of suitable solvents are alcohols, such as methanol, ethanol, n-propanol, isopropanol, n-butanol, sec-butanol, tert-butanol, n-hexanol and cyclohexanol, and also glycols, such as ethylene glycol, propylene glycol and butylene glycol, and the methyl or ethyl ethers of dihydric alcohols, diethylene glycol, triethylene glycol, glycerol and dioxane.

Preference is given to polymers obtainable by free-radical polymerization of
1) 3 to 30% by weight of at least one monomer containing quaternary amino groups (a1) and
2) 0 to 15% by weight of one or more further copolymerizable monomers (c) and
3) 0 to 15% by weight of one or more further copolymerizable monomers (d) in the presence of
4) 70 to 97% by weight of at least one polyether-containing compound, where, for a defined polymerization, the percentages by weight of the individual components a1-d add up in each case to 100% by weight.

Particular preference is given to polymers obtainable by free-radical polymerization of
1) 4 to 12% by weight of at least one monomer containing quaternary amino groups (a1) and
2) 0% by weight of one or more further copolymerizable monomers (c)
3) 0% by weight of one or more further copolymerizable monomers in (d) the presence of
4) 88 to 96% by weight of at least one polyether-containing compound, where, for a defined polymerization, the percentages by weight of the individual components a1 and b add up in each case to 100% by weight.

The K values of the polymers should be in the range from 10 to 300, preferably 11 to 100, particularly preferably 15 to 60. The K value desired in each case can be established in a manner known per se through the composition of the feed materials. The K values are determined in accordance with Fikentscher, Cellulosechemie, Vol. 13, pp. 58 to 64, and 71 to 74 (1932) in N-methylpyrrolidone at 25° C. and polymer concentrations which, depending on the K value range, are between 0.1% by weight and 5% by weight. It is also possible to use other solvents in place of N-methylpyrrolidone. Particular preference is given to ethanol. The abovementioned limits preferably refer to the determination of 1% strength polymer solutions in ethanol.

After the reaction, the polymer solutions can be subjected to steam distillation to remove, for example, residual monomers. After the steam distillation, aqueous solutions or dispersions are obtained depending on the amount of the quaternized amino groups and the nature of the polyethers (b). It is preferable to obtain aqueous solutions. Advantageously, water is added to the polymers according to the invention for reasons of better handleability when the polymerization is complete. In this connection, the content of polymer is preferably 20 to 60% by weight.

The polymers can be converted into powder form by various drying processes, such as, for example, spray drying, fluidized spray drying, roll drying or freeze drying. The drying process preferably used is spray drying. The dry polymer powders obtained in this way can be dissolved or redispersed in water again to prepare an aqueous solution or dispersion, respectively. Conversion into powder form has the advantage of better storage stability, simpler transportation option and a lower tendency for microbial attack.

The water-soluble or water-dispersible polyether-containing polymers according to the invention can advantageously be used for numerous purposes. Examples which may be mentioned are a use a) in cosmetic preparations
b) in medicaments and other therapeutic-medicinal preparations
c) in formulations for cleaners, disinfectants or dishwashing detergents
d) in textile and/or carpet care compositions e.g. in fabric softeners or in laundry detergents and care compositions
e) as stabilizers for, for example, dispersions, e.g. when polymerizations are carried out in aqueous solution or emulsion
f) as stabilizer for the preparation of photographic emulsions
g) as flocculants, for example in wastewater treatment
h) as auxiliaries for papermaking, in particular for the production of papers for use in inkjet processes
i) in the dyeing industry as additive for dyes or inks
j) as humectant or gel former
k) as gelatin replacement
l) as thickener
m) as dehydrogenation agent The water-soluble or water-dispersible polyalkylene oxide- or polyglycerol-containing polymers according to the invention are particularly suitable for use in cosmetic formulations, in particular hair cosmetic formulations.

The term "cosmetic formulations" is to be understood in broad terms and means all of those preparations which are suitable for application to skin and/or hair and/or nails and have a purpose which is not exclusively medicinal-therapeutic.

Hair cosmetic formulations include, in particular, styling compositions and/or conditioners in hair cosmetic preparations such as hair treatments, hair mousses, hair gels or hairsprays, hair lotions, hair rinses, hair shampoos, hair emulsions, hair-end fluids, neutralizers for permanent waves, hair colorants and bleaches, hot-oil treatment preparations, conditioners, setting lotions or hairsprays. Depending on the field of application, the hair cosmetic preparations can be applied in the form of (aerosol) spray, (aerosol) mousse, gel, gel spray, cream, lotion or wax.

Further cosmetic preparations include, for example, conditioners for the skin, e.g. in skin or bodycare compositions, foam baths and shower preparations. Also covered is the use in oral hygiene and other hygiene formulations, in anti-acne compositions, in sunscreens, in tanning compositions, in pigment-containing formulations in decorative cosmetics, in anti-wrinkle compositions, in skin-firming compositions, and in deodorants.

The hair cosmetic formulations according to the invention comprise, in a preferred embodiment, a) 0.05-20% by weight of the polymer according to the invention
b) 20-99.95% by weight of water and/or alcohol
c) 0-79.5% by weight of further constituents.

Alcohol is to be understood as meaning all alcohols customary in cosmetics, e.g. ethanol, isopropanol, n-propanol.

Further constituents are to be understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances such as panthenol, collagen, vitamins, protein hydrolyzates, alpha- and beta-hydroxycarboxylic acids, protein hydrolyzates, stabilizers, pH regulators, dyes, viscosity regulators, gel formers, dyes, salts, humectants, refatting agents, complexing agents and further customary additives.

Also included here are all styling and conditioning polymers known in cosmetics which can be used in combination with the polymers according to the invention if very specific properties are to be established.

Examples of suitable conventional hair cosmetic polymers are anionic polymers. Such anionic polymers are homo- and copolymers of acrylic acid and methacrylic acid or salts thereof, copolymers of acrylic acid and acrylamide and salts thereof; sodium salts of polyhydroxycarboxylic acids, water-soluble or water-dispersible polyesters, polyurethanes (Luviset® P.U.R.) and polyureas. Particularly suitable polymers are copolymers of t-butyl acrylate, ethyl acrylate, methacrylic acid (e.g. Luvimer® 100P), copolymers of N-tert-butylacrylamide, ethyl acrylate, acrylic acid (Ultrahold® 8, Strong), copolymers of vinyl acetate, crotonic acid and optionally further vinyl esters (e.g. Luviset® grades), maleic anhydride copolymers, optionally reacted with alcohols, anionic polysiloxanes, e.g. carboxyfunctional ones, copolymers of vinylpyrrolidone, t-butyl acrylate, methacrylic acid (e.g. Luviskol® VBM).

In addition, the group of polymers suitable for combination with the polymers according to the invention includes, by way of example, Balance® CR (National Starch; acrylate copolymer), Balance® 0/55 (National Starch; acrylate copolymer), Balance® 47 (National Starch; octylacrylamide/acrylate/butylaminoethyl methacrylate copolymer), Aquaflex® FX 64 (ISP; isobutylene/ethylmaleimide/hydroxyethylmaleimide copolymer), Aquaflex® SF-40 (ISP/National Starch; VP/vinylcaprolactam/DMAPA acrylate copolymer), Alliance® LT-120 (ISP/Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid) in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Acudyne® 258 (Rohm & Haas; acrylate/hydroxy ester acrylate copolymer), Luviset® PUR (BASF, polyurethane-1), Luviflex® Silk (BASF), Eastman® AQ48 (Eastman).

Very particularly preferred anionic polymers are acrylates with an acid number greater than or equal to 120 and copolymers of t-butyl acrylate, ethyl acrylate, methacrylic acid.

Further suitable hair cosmetic polymers are cationic polymers with the designation polyquaternium in accordance with INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam N-vinylpyrrolidone/N-vinylimidazolium salts (Luviquat® Hold); cationic cellulose derivatives (polyquaternium-4 and -10), acrylamide copolymers (polyquaternium-7).

In addition, it is possible to use cationic guar derivatives, such as guar hydroxypropyltrimonium chloride (INCI).

Further suitable hair cosmetic polymers are also neutral polymers, such as polyvinylpyrrolidones, copolymers of N-vinylpyrrolidone and vinyl acetate and/or vinyl propionate, polysiloxanes, polyvinylcaprolactam and copolymers containing N-vinylpyrrolidone, polyethyleneimines and salts thereof, polyvinylamines and salts thereof, cellulose derivatives, polyaspartic acid salts and derivatives.

To establish certain properties, the preparations may also additionally comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and amino-functional silicone compounds such as amodimethicones (CTFA).

The polymers according to the invention are particularly suitable as setting agents in hairstyling preparations, in particular hairsprays (aerosol sprays and pump sprays without propellant gas) and hair mousses (aerosol mousses and pump mousses without propellant gas).

In a preferred embodiment, these preparations comprise a) 0.1-10% by weight of the polymer according to the invention b) 20-99.9% by weight of water and/or alcohol c) 0-70% by weight of a propellant d) 0-20% by weight of further constituents.

Propellants are the propellants customarily used for hairsprays or aerosol mousses. Preference is given to mixtures of propane/butane, pentane, dimethyl ether, 1,1-difluoroethane (HFC-152 a), carbon dioxide, nitrogen or compressed air.

A formulation for aerosol hair mousses which is preferred in accordance with the invention comprises a) 0.1-10% by weight of the polymer according to the invention b) 55-94.8% by weight of water and/or alcohol c) 5-20% by weight of a propellant d) 0.1-5% by weight of an emulsifier e) 0-10% by weight of further constituents.

The emulsifiers used may be any emulsifiers customarily used in hair mousses. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether; ceteareths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimoniumchloride, cetyltrimonium bromide, cocotrimonium methylsulfate, quaternium-1 to x (INCI).

Anionic emulsifiers may be chosen, for example, from the group of alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation which is suitable according to the invention for styling gels may, for example, have the following composition:

a) 0.1-10% by weight of the polymer according to the invention b) 60-99.85% by weight of water and/or alcohol c) 0.05-10% by weight of a gel former d) 0-20% by weight of further constituents.

Gel formers which may be used are all gel formers customary in cosmetics. These include slightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, polyquaternium-32 (and) Paraffinum Liquidum (INCI), sodium acrylates copolymer (and) Paraffinum Liquidum (and) PPG-1 Trideceth-6, acrylamidopropyltrimonium chloride/acrylamide copolymer, steareth-10 allyl ether acrylates copolymer, polyquaternium-37 (and) Paraffinum Liquidum (and) PPG-1 Trideceth-6, polyquaternium 37 (and) propylene glycol dicapratedicaprylate (and) PPG-1 Trideceth-6, polyquaternium-7, polyquaternium-44.

The polymers according to the invention can also be used in shampoo formulations as setting and/or conditioning agents. Suitable conditioning agents are, in particular, polymers with cationic charge. Preferred shampoo formulations comprise a) 0.05-10% by weight of the polymer according to the invention b) 25-94.95% by weight of water c) 5-50% by weight of surfactants c) 0-5% by weight of a further conditioning agent d) 0-10% by weight of further cosmetic constituents.

In the shampoo formulations, it is also possible to use all anionic, neutral, amphoteric or cationic surfactants customarily used in shampoos.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Suitable examples are sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, it is possible to use cocodimethylsulfopropylbetaine, laurylbetaine, cocamidopropylbetaine or sodium cocamphopropionate.

Examples of suitable nonionic surfactants are the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mols per mole of alcohol. Also suitable are alkylamine oxides, mono- or dialkylalkanolamides, fatty acid esters of polyethylene glycols, alkyl polyglycosides or sorbitan ether esters.

Furthermore, the shampoo formulations may comprise customary cationic surfactants, such as, for example, quaternary ammonium compounds, for example cetyltrimethylammonium chloride.

To achieve certain effects, customary conditioning agents can be used in combination with the polymers according to the invention, in the shampoo formulations. These include, for example, cationic polymers having the designation Polyquaternium in accordance with INCI, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). It is also possible to use protein hydrolyzates, and conditioning substances based on silicone compounds, for example polyalkylsiloxanes, polyarylsiloxanes, polyarylalkylsiloxanes, polyether siloxanes or silicone resins. Further suitable silicone compounds are Dimethicone Copolyols (CTFA) and aminofunctional silicone compounds such as Amodimethicone (CTFA). It is also possible to use cationic guar derivatives, such as guar hydroxypropyltrimonium chloride (INCI).

WORKING EXAMPLES

The examples below demonstrate the improved properties of the polymers according to the invention compared with polymers in which either water was present in the reaction mixture in relatively large amounts or for which the polyether component was only added after polymerization of the individual monomers.

The following were used:
a) vinylimidazole quaternized with dimethyl sulfate, 45% strength solution in water (subsequently "QVIXDMS")
b) diallyldimethylammonium chloride, 65% strength solution in water (subsequently "DADMAC")
c) Pluronic® PE 4300 polyethylene glycol-polypropylene glycol block copolymer (BASF Aktiengesellschaft)
d) Pluriol® E 600 polyethylene glycol with molecular weight 600 (BASF Aktiengesellschaft)
e) Wako V 50 Azo initiator from Wako Chemicals GmbH Example 1

Preparation of a Cationic Polymer in Accordance with the Process of the Invention A cationic polymer with the quantitative composition Pluronic PE 4300:QVIxDMS:DADMAC=92:7:1 was prepared. The monomers (a1) used ere QVIxDMS and DADMAC in the ratio 7:1. The water content during the polymerization was 7% by weight.

|  |  |  | Feed substance conc. |
|---|---|---|---|
| Initial charge | Pluronic PE 4300 | 152.3 g | 100% |
|  | Feed 1 | 8.0 g |  |
| Feed 1 | QVIxDMS 45% | 26.2 g | 45% |
|  | DADMAC 65% | 2.6 g | 65% |
| Feed 2 | Pluriol E 600 | 30.0 g | 100% |
|  | tert-butyl peroxyethyl hexanoate | 1.35 g | 100% |
| Feed 3 | Demin. water | 120.0 g | 100% |

The reaction was carried out in a 2 l glass apparatus (HWS) with anchor stirrer and temperature control (internal). The initial charge was introduced with the liquid product Pluronic PE 4300 and some of feed 1 and then heated to 85° C. At 80° C., 8 g of feed 2 were added and the mixture was then left for 4 minutes. Feeds 1 and 2 were then started simultaneously. Feed 1 was added over 6 h, and feed 2 was added in parallel thereto, also over 6 h. The mixture was then after-polymerized for 2 h at 85° C. The mixture was then cooled to room temperature and diluted with feed 3. For an assessment of the properties see below.

Comparative Example 1

Preparation of a Cationic Polymer by Polymerization in Aqueous Solution

A cationic polymer with the quantitative composition Pluronic PE 4300:QVIxDMS:DADMAC=92:7:1 was prepared. The quantitative composition was identical to that in example 1. The monomers (a1) used were QVIxDMS and DADMAC in the ratio 7:1. The water content during the polymerization was, however, 50% by weight, in contrast to example 1.

|  |  |  | Feed substance conc. |
|---|---|---|---|
| Initial charge | Pluronic PE 4300 | 152.3 g | 100% |
|  | Feed 1 | 8.0 g |  |
|  | Demin. water | 185.0 g | 100% |
| Feed 1 | QVIxDMS 45% | 26.2 g | 45% |
|  | DADMAC 65% | 2.6 g | 65% |
| Feed 2 | Pluriol E 600 | 30.0 g | 100% |
|  | tert-butyl peroxyethyl-hexa-noate | 1.35 g | 100% |

The polymerization was carried out analogously to that described by example 1. The reaction was carried out in a 2 l glass apparatus (HWS) with anchor stirrer and temperature control (internal). The initial charge was introduced with the liquid product Pluronic PE 4300, water and part of feed 1 and then heated to 85° C. At 80° C., 8 g of feed 2 were added, and then the mixture was left for 4 minutes. Feeds 1 and 2 were then started simultaneously. Feed 1 was added over 6 h, and feed 2 was added in parallel thereto, also over 6 h. The mixture was then after-polymerized for 2 h at 85° C. The mixture was then cooled to room temperature. For an assessment of the properties, see below.

Comparative Example 2

Preparation of a Mixture of Polyether and a Cationic Polymer a) A cationic polymer with the quantitative composition QVIxDMS:DADMAC=92:7:1 was prepared. This serves as preproduct for the preparation of the mixture containing the polyether component. The quantitative composition was identical to that of the monomers (a1) in example 1. The monomers (a1) used were QVIxDMS and DADMAC in the ratio 7:1.

|  |  |  | Feed substance conc. |
|---|---|---|---|
| Initial charge | Feed 1 | 12.0 g |  |
|  | Demin. water | 230.0 g | 100% |
| Feed 1 | QVIxDMS 45% | 60.9 g | 45% |
|  | DADMAC 65% | 6.02 g | 65% |
| Feed 2 | Demin. water | 20.0 g | 100% |
|  | Wako V50 | 0.65 g | 100% |

The reaction was carried out in a 2 l glass apparatus (HWS) with anchor stirrer and temperature control (internal). The initial charge was introduced with water and part of feed 1 and then heated to 75° C. At 70° C., 2 g of feed 2 were added and then the mixture was left for 3 minutes. Feeds 1 and 2 were then started simultaneously. Feed 1 was added over 2.5 h, and feed 2 was added over 3 h. The mixture was then after-polymerized at 75° C. for 3 h. The mixture was then cooled to room temperature. For an assessment of the properties of the cationic preduct, see below.

b) A mixture of the aqueous, cationic polymeric preproduct (see above) and Pluronic PE 4300 with the formal composition as in example 1 or comparative example 1 was prepared. The composition was Pluronic PE 4300: QVIxDMS:DADMAC=92:7:1.

|  |  |  | Feed substance conc. |
|---|---|---|---|
| Initial charge | Pluronic PE 4300 | 92.0 g | 100% |
|  | cat. | 74.4 g | 10.8% |
|  | Pluriol E 600 | 18.1 g | 100% |
|  | Demin. water | 100 g | 100% |

The mixing was carried out in a 2 l glass apparatus (HWS) with anchor stirrer and temperature control (internal). As well as the products Pluronic PE 4300 and Pluriol E 600, the cationic preproduct from the preceding experiment was introduced into the initial charge. This initial charge is mixed vigorously at room temperature. For an assessment of the properties, see below.

Comparative Example 3

Reworking of Example 2 from U.S. Pat. No. 4,048,301

Example 2 from U.S. Pat. No. 4,048,301 was reworked as described therein. For this purpose, the following starting materials were introduced into a 500 ml round-bottomed flask with mechanical stirrer, reflux condenser and thermometer:

| N-vinylpyrrolidone, freshly distilled | 54.62 g |
|---|---|
| dimethylaminoethyl methacrylate | 9.87 g |
| dimethylaminoethyl methacrylate quaternized with dimethyl sulfate | 26.70 g |
| polyethylene glycol, MW-20,000 | 8.81 g |
| azobisisobutyronitrile | 0.2 g |
| ethanol, absolute | 20 g |

The reaction mixture was heated to 65° C. with stirring. As soon as the mixture becomes viscous, 80 g of abs. ethanol preheated to 65° C. are again added. The temperature is then increased to 76° C. and maintained at that for 24 h with stirring. 200 g of water are then added and the water-ethanol azeotrope is distilled off until all of the ethanol has been removed.

Example 2

Comparison of the Properties of the Polymers According to the Invention with the Polymers from Comparative Examples 1, 2 and 3

The polymers were used in a surfactant solution formulation with the following composition:
40.0% of Texapon NSO (sodium laureth sulfate solution 28%; Cognis)
10.0% of Tego-Betaine L7 (cocamidopropylbetaine solution 30%; Goldschmidt).
0.5% of polymer (solids content)
add 100% of water i) Determination of the Combability The following working instruction describes the procedure for determining the wet and dry combability of hair following treatment with conditioners. All measurements are carried out in a climatically controlled room at 65% relative humidity and 21° C.

Instruments Used

Wet combability: Frank tensile/pressure tester

Dry combability: Diastron force measurement system

Digital balance (top-pan balance)

Hair:
a) European, bleached: hair tresses from Wernesgrün (bleaching see below)
b) Asiatic, untreated: hair tresses from Wernesgrün with split ends The following tests are carried out:
Wet combability following shampoo application to European bleached hair
Dry combability following shampoo application to Asiatic hair Pretreatment/Cleansing of the Hair:

Prior to first use, the Asiatic hair tresses are cleansed in a solvent mixture (ethanol/isopropanol/acetone/water 1:1:1:1) until the hair looks clean in the dry state (i.e. no longer sticks together). The hair is then washed with sodium lauryl ether sulfate.

The European hair is then treated with a bleaching paste (7.00 g of ammonium carbonate, 8.00 g of calcium carbonate, 0.50 g of Aerosil 200, 9.80 g of hydrogen peroxide (30% strength), 9.80 g of demineralized water). The hair tresses are completely immersed in the bleaching paste, thus ensuring extensive wetting of the overall surface of the hair. The tresses are then wiped between the fingers in order to remove excess bleaching paste. The contact time of the remaining bleaching agent on the hair is matched to the degree of damage required, and is usually 15 to 30 minutes, but can vary depending on the hair quality. Thereafter, the bleached hair tresses are rinsed thoroughly under running tap water (2 minutes) and washed with sodium lauryl ether sulfate. Due to "insidious" bleaching, the hair should then be immersed briefly into an aqueous acidic solution (e.g. citric acid) and then washed again with tap water.

Applications:

In the hair is immersed for 1 minute in the surfactant formulation to be tested, shampooed for 1 minute and then rinsed for 1 minute under running drinking water (hand-hot).

I) Wet Combability

Determination of blank value for wet combability: The washed hair is dried overnight in a climatically controlled room. Prior to measurement, it is shampooed twice using Texapon NSO for a total of 1 minute and rinsed for 1 minute, such that it is definitely wet, i.e. swollen. Prior to the start of the measurement, the tress is combed beforehand until knots are no longer present in the hair and thus a constant application of force is required for repeated measurement combing. The tress is then fixed into the holder and, using the fine-toothed side of the comb, is combed into the fine-toothed side of the test comb. The insertion of the hair into the test comb has to be carried out uniformly and free from tension for each measurement. The measurement is started and evaluated by means of software (EGRANUDO program, Frank). The individual measurement is repeated 5 to 10 times. The calculated average is noted.

Determination of measurement value for wet combability: Following the determination of the blank value, the hair is treated in each case according to the desired application. The combing force is measured analogously to the blank value determination.

Evaluation:

$$\text{Combing force decrease wet}[\%] = 100 - (\text{measurement value} * 100/\text{blank value})$$

II) Dry Combability

Determination of blank value for dry combability: The washed hair is dried overnight in a climatically controlled room. Prior to the start of the measurement, the tress is combed beforehand so that knots are no longer present in the hair and thus a constant application of force is required for repeated measurement combing. The tress is then fixed to the holder and combed into the fine-toothed side of the test comb. The insertion of the hair into the test comb has to be carried out uniformly and free from tension for each measurement. The measurement is started and evaluated by means of software (mtt-win, DIASTRON). The individual measurement is repeated 5 to 10 times. The calculated average is noted together with the standard deviation.

Determination of the measurement value for dry combability: Following the determination of the blank value, the hair is treated in each case according to the desired application and dried overnight. The combing force is measured analogously to the blank value determination. Evaluation:

$$\text{Combing force decrease wet}[\%] = 100 - (\text{measurement value} * 100/\text{blank value})$$

The polymer according to the invention produces excellent results with regard to dry combability, but in particular with regard to wet combability. A further advantage is that, with the polymer according to the invention, clear (washing) formulations are also possible. The polymer described in U.S. Pat. No. 4,048,301 (comparison 3) is superior to comparative examples 1 and 2, but significantly inferior to the polymer according to the invention.

|  | Example 1 | Comparison 1 | Comparison 2a | Comparison 2b | Comparison 3 |
|---|---|---|---|---|---|
| Solids content (% by wt.) | 60.2 | 49.8 | 10.8 | 60.8 | 37.2 |
| Combing force decrease wet (%) (Europ. hair) | 44 | 23 | 15 | 18 | 28 |
| Combing force decrease dry (%) (Asiat. hair) | 86 | 77 | ND | ND | 79 |
| Surfactant solution 0.5% active ingredient | clear | clear | slightly cloudy | clear | clear |
| K value 1% in ethanol | 15.1 |  |  |  |  |

ND: Not determined since combing force decrease wet insufficient (<20%)

We claim:

1. A cosmetic preparation comprising a cationic polymer which is produced by the process comprising:
polymerizing in a polymerization vessel from 3 to 30% by weight of at least one quaternary nitrogen-comprising free-radically polymerizable monomer (a1) and/or a direct preproduct (a2) thereof,
from 0 to 15% by weight of one or more first additional free-radically polymerizable monomer (c) having a solubility in water above 60 g/l at 25° C. and
from 0 to 15% by weight of one or more second additional free-radically polymerizable monomer (d) having a solubility in water of less than 60 g/l at 25° C.,
in the presence of from 70 to 97% by weight of at least one polyether-comprising compound (b),
wherein
the at least one quaternary nitrogen-comprising free-radically polymerizable monomer (a1) and/or a direct preproduct (a2) thereof is at least one selected from the group consisting of 3-methyl-1-vinylimidazolium chloride, 3-methyl-1-vinylimidazolium methylsulfate and N,N-dimethyl-N,N-diallylammonium chloride,
the polyether-comprising compound (b) is a polymer, copolymer or block copolymer of at least one compound selected from the group consisting of ethylene oxide and propylene oxide,
the water content in the reaction mixture during the polymerization is less than 10% by weight;
if the polymerization vessel comprises the preproduct (a2), said preproduct (a2) is converted at least partially into a compound comprising quaternary nitrogen (a2') subsequently to or during said polymerizing;
the molar ratio of the sum of the at least one quaternary nitrogen-comprising free-radically polymerizable monomer (a1), the compound comprising quaternary nitrogen (a2') and the one or more first additional free-radically polymerizable monomer (c) to the sum of the one or more second additional free-radically polymerizable monomer (d) is at least 2 to 1; and
the percentages by weight of the at least one quaternary nitrogen-comprising free-radically polymerizable monomer (a1) and/or a direct preproduct (a2) thereof, the at least one polyether-comprising compound (b), the one or more first additional free-radically polymerizable monomer (c) and the one or more second additional free-radically polymerizable monomer (d) add up in each case to 100% by weight.

2. The cosmetic preparation as claimed in claim 1, wherein the at least one quaternary nitrogen-comprising free-radically polymerizable monomer (a1) comprises a mixture of 3-methyl-1-vinylimidazolium methylsulfate and N,N-dimethyl-N,N-diallylammonium chloride.

3. The cosmetic preparation as claimed in claim 1, wherein said conversion of the preproduct (a2) to the compound comprising quaternary nitrogen (a1) occurs in the presence of an alkyl halide having 1 to 24 carbon atoms, a dialkyl sulfate having 1 to 24 carbon atoms, an alkylene oxide or an epichlorohydrin.

4. The cosmetic preparation as claimed in claim 1, wherein said conversion of the preproduct (a2) to the compound comprising quaternary nitrogen (a1) occurs in the presence of a trialkylamine.

5. The cosmetic preparation as claimed in claim 1, wherein the one or more first additional free-radically polymerizable monomer (c) is selected from the group consisting of N-vinyllactams, N-vinylcarboxamides, hydroxyalkyl acrylates, ethylenically unsaturated amides, vinylimidazoles, unsaturated acids and unsaturated amines.

6. The cosmetic preparation as claimed in claim 1, wherein the one or more first additional free-radically polymerizable monomer (c) is selected from the group consisting of N-vinylpyrrolidone, N-vinylpiperidone, N-vinylcaprolactam, N-vinylformamide, N-ethyl-N-vinylacetamide or N-methyl-N-vinylacetamide, 2-hydroxyethyl acrylate, 2-hydroxyethyl methacrylate, 2-hydroxypropyl methacrylate, butanediol monoacrylate, acrylamide, methacrylamide, N-vinylimidazole, acrylic acid, maleic acid, methacrylic acid, 2-acrylamido-2-methylpropanesulfonic acid, dimethylaminoethyl acrylate and dimethylamino methacrylate.

7. The cosmetic preparation as claimed in claim 1, wherein the one or more second additional free-radically polymerizable monomer (d) is selected from the group consisting of $C_1$-$C_{10}$-alkyl esters of monoethylenically unsaturated $C_3$-$C_6$-carboxylic acids, di-$C_1$-$C_{10}$-alkyl esters of ethylenically unsaturated dicarboxylic acids, hydrocarbons having at least one free-radically polymerizable carbon-carbon double bond, vinyl, vinylidene or allyl halides, vinyl, allyl and methallyl esters of $C_1$-$C_{40}$ linear, $C_3$-$C_{40}$ branched-chain or $C_3$-$C_{40}$ carbocyclic carboxylic acids of aliphatic, saturated and unsaturated nature, vinyl, allyl and methallyl ethers of linear or branched, aliphatic alcohols having 2 to 20 carbon atoms.

8. The cosmetic preparation as claimed in claim 1, wherein the one or more second additional free-radically polymerizable monomer (d) is selected from the group consisting of methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl acrylate, stearyl (meth)acrylate, preferably styrene, alpha-methylstyrene, tert-butylstyrene, butadiene, isoprene, cyclohexadiene, ethylene, propylene, 1-butene, 2-butene, isobutylene, vinyltoluene, vinyl chloride, vinylidene chloride, allyl chloride, vinyl acetate, vinyl propionate, vinyl butyrate, vinyl valerate, vinyl hexanoate, vinyl 2-ethylhexanoate, vinyl decanoate, vinyl laurate, vinyl stearate, vinyl methyl ether, vinyl ethyl ether, vinyl dodecyl ether, vinyl hexadecyl ether, vinyl stearyl ether, acrylamidoglycolic acid, fumaric acid and crotonic acid.

9. The cosmetic preparation as claimed in claim 1, wherein
the polyether-comprising compound (b) has an average molecular weight of from 500 to 50 000 (number-average).

10. The cosmetic preparation as claimed in claim 1, wherein the polyether-comprising compound (b) is a polymer, copolymer or block copolymer of ethylene oxide and a content of ethylene oxide is from 9 to 99 mole %.

11. The cosmetic preparation as claimed in claim 1, wherein
the percentages by weight of the at least one quaternary nitrogen-comprising free-radically polymerizable monomer (a1), the at least one polyether-comprising compound (b), the one or more first additional free-radically polymerizable monomer (c) and the one or more second additional free-radically polymerizable monomer (d) add up to 100% by weight.

12. The cosmetic preparation as claimed in claim 1,
wherein the cationic polymer is produced by polymerizing 4-12% by weight of
the at least one quaternary nitrogen-comprising free-radically polymerizable monomer a1) in the presence of from 88-96% by weight of the at least one polyether-comprising compound b)
and the percentages by weight of the at least one quaternary nitrogen-comprising free-radically polymerizable monomer (a1) and the at least one polyether-comprising compound (b) add up to 100% by weight.

13. A cationic polymer produced by the process comprising:
polymerizing in a polymerization vessel:
from 3 to 30% by weight of at least one cationic, quaternary, free-radically polymerizable monomer (a1)
from 0 to 15% by weight of one or more first additional free-radically polymerizable monomer (c) having a solubility in water above 60 g/l at 25° C. and
from 0 to 15% by weight of one or more second additional free-radically polymerizable monomer (d) having a solubility in water below 60 g/l at 25° C.,
in the presence of from 70 to 97% by weight of at least one polyether-comprising compound (b),
wherein
the at least one quaternary nitrogen-comprising free-radically polymerizable monomer (a1) and/or a direct pre-product (a2) thereof is at least one selected from the group consisting of 3-methyl-1-vinylimidazolium chloride, 3-methyl-1-vinylimidazolium methylsulfate and N,N-dimethyl-N,N-diallylammonium chloride,
the polyether-comprising compound (b) is a polymer, copolymer or block copolymer of at least one compound selected from the group consisting of ethylene oxide and propylene oxide,
the molar ratio of the sum of the at least one cationic, quaternary, free-radically polymerizable monomer (a1) and the one or more further free-radically polymerizable monomer (c) to the sum of the one or more second additional free-radically polymerizable monomer (d) is at least 2 to 1,
the water content in the reaction mixture during the polymerization is less than 10% by weight, and
the percentages by weight of the at least one cationic, quaternary, free-radically polymerizable monomer (a1), at least one polyether-comprising compound (b), the one or more further free-radically polymerizable monomer (c) and the one or more second additional free-radically polymerizable monomer (d) add up to 100% by weight.

14. A process for the preparation of cationic polymers as claimed in claim 13, the process comprising:
polymerizing from 3 to 30% by weight of at least one cationic, quaternary free-radically polymerizable monomer (a1) in the presence of
from 70 to 97% by weight of at least one polyether-comprising compound (b)
from 0 to 15% by weight of one or more first additional free-radically polymerizable monomer (c) having a solubility in water of more than 60 g/l at 25° C. and optionally
from 0 to 15% by weight of one or more second additional free-radically polymerizable monomer (d) having a solubility in water of less than 60 g/l at 25° C.,
wherein the molar ratio of the sum of the at least one cationic, quaternary free-radically polymerizable monomer (a1) and the one or more first additional free-radically polymerizable monomer (c) to the sum of the one or more second additional free-radically polymerizable monomer (d) is at least 2 to 1,
the water content in the reaction mixture during the polymerization is less than 10% by weight, and
the percentages by weight of the at least one cationic, quaternary free-radically polymerizable monomer (a1), the at least one polyether-comprising compound (b), the one or more first additional free-radically polymerizable monomer (c), and the one or more second additional free-radically polymerizable monomer (d) add up to 100% by weight.

15. A hair cosmetic formulation comprising:
a) 0.05-20% by weight of the cosmetic preparation as claimed in claim 1,
b) 20-99.95% by weight of water and/or alcohol and
c) 0-79.05% by weight of additional constituents.

16. A hair cosmetic formulation comprising:
a) 0.1-10% by weight of the cosmetic preparation as claimed in claim 1,
b) 20-99.9% by weight of water and/or alcohol
c) 0-70% by weight of a propellant and
d) 0-20% by weight of additional constituents.

17. A hair cosmetic formulation comprising:
a) 0.1-10% by weight of the cosmetic preparation as claimed in claim 1,
b) 55-94.8% by weight of water and/or alcohol
c) 5-20% by weight of a propellant
d) 0.1-5% by weight of an emulsifier and
e) 0-10% by weight of additional constituents.

18. A hair cosmetic formulation comprising:
a) 0.1-10% by weight of the cosmetic preparation as claimed in claim 1,
b) 60-99.85% by weight of water and/or alcohol
c) 0.05-10% by weight of a gel former and
d) 0-20% by weight of additional constituents.

19. A hair cosmetic formulation comprising:
a) 0.05-10% by weight of the cosmetic preparation as claimed in claim 1,
b) 25-94.95% by weight of water
c) 5-50% by weight of surfactants
d) 0-5% by weight of a conditioning agent and
e) 0-10% by weight of additional cosmetic constituents.

* * * * *